(12) United States Patent
Norris (10) Patent No.: US 11,389,606 B2
(45) Date of Patent: Jul. 19, 2022

(54) COMPACT FLUID MOVING ASSEMBLY AND DEVICE EMPLOYING SAME

(71) Applicant: KONINKLIJKE PHILIPS N.V., Eindhoven (NL)

(72) Inventor: Russell Hughes Norris, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 458 days.

(21) Appl. No.: 16/455,913

(22) Filed: Jun. 28, 2019

(65) Prior Publication Data

US 2020/0001029 A1 Jan. 2, 2020

Related U.S. Application Data

(60) Provisional application No. 62/691,647, filed on Jun. 29, 2018.

(51) Int. Cl.
*A61M 16/00* (2006.01)
*F04D 17/08* (2006.01)
*F04D 25/06* (2006.01)

(52) U.S. Cl.
CPC .... *A61M 16/0066* (2013.01); *A61M 16/0003* (2014.02); *F04D 17/08* (2013.01); *F04D 25/06* (2013.01); *A61M 2016/0027* (2013.01)

(58) Field of Classification Search
CPC .............................. A61M 16/055; F04D 17/08
See application file for complete search history.

(56) References Cited

U.S. PATENT DOCUMENTS

| | | | |
|---|---|---|---|
| 8,708,674 B2 | 4/2014 | Hoffman | |
| 8,973,576 B2 | 3/2015 | Kenyon | |
| 9,404,504 B2 | 8/2016 | Sakai | |
| 9,662,463 B2 | 5/2017 | Kenyon | |
| 9,677,563 B2 | 6/2017 | Kenyon | |
| 2005/0188989 A1 | 9/2005 | Delache | |
| 2007/0247009 A1 | 10/2007 | Hoffman | |
| 2014/0105744 A1 | 4/2014 | Yasuda | |
| 2014/0158131 A1 | 6/2014 | Kenyon | |
| 2017/0002830 A1 | 1/2017 | Bothma | |
| 2018/0064894 A1 | 3/2018 | Fu | |
| 2019/0134329 A1* | 5/2019 | Kuriger | ............... F04D 29/4253 |
| 2019/0160240 A1 | 5/2019 | Bothma | |

* cited by examiner

*Primary Examiner* — Margaret M Luarca (57) ABSTRACT

An assembly for moving a fluid includes: a housing having an inlet and an outlet; a first shaft member fixedly coupled to the housing, the first shaft member having a central axis; a stator assembly fixedly coupled to the housing, disposed around the central axis and spaced radially outward from the first shaft member; and a driven assembly. The driven assembly includes: a second shaft member having a first end, a second end, and a cylindrical cavity defined therein extending inward from the first end; a magnetic ring fixedly coupled to the second shaft member at or about the first end; and an arrangement fixedly coupled to the second shaft member at or about the second end. A bearing system is disposed between the first shaft member and the second shaft member such that the driven assembly is rotatably coupled to the first shaft member.

20 Claims, 6 Drawing Sheets

COMPACT FLUID MOVING ASSEMBLY AND DEVICE EMPLOYING SAME

BACKGROUND OF THE INVENTION

1. Field of the Invention

The present invention pertains to assemblies for moving fluids and, more particularly, to assemblies for moving gases. Even more particularly, the present invention pertains to assemblies for moving treatment gases in devices used for providing treatment gas to the airway of a user.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Innovations are continuously being made to improve the comfort of patient interface devices, and thus improve patient compliance. Additionally, a need exists for improved pressure generating devices and blowers for use therein which can provide suitable supplies of treatment gas in as quiet and compact of manner as possible.

SUMMARY OF THE INVENTION

Accordingly, it is an object of the present invention to overcome shortcomings of conventional pressure generating devices and blowers for use therein.

As one aspect of the present invention an assembly for moving a fluid is provided. The assembly comprises: a housing having an inlet and an outlet defined therein; a first shaft member fixedly coupled to the housing, the first shaft member having a central axis; and a stator assembly fixedly coupled to the housing, disposed around the central axis and spaced radially outward from the first shaft member. The assembly further comprises a driven assembly comprising: a second shaft member having a first end, a second end disposed opposite the first end, and a cylindrical cavity defined therein which extends inward from the first end; a magnetic ring fixedly coupled to the second shaft member at or about the first end; and an arrangement fixedly coupled to the second shaft member at or about the second end. The assembly also comprises a bearing system disposed between the first shaft member and the second shaft member such that the driven assembly is rotatably coupled to the first shaft member. The driven assembly is structured to be rotated about the central axis via magnetic interactions between the stator assembly and the magnetic ring, and the arrangement is structured to cause movement of a fluid into the inlet of the housing and out from the outlet of the housing.

The arrangement may comprise an impeller structured to cause movement of a gas.

The housing may comprise a first housing portion and a second housing portion coupled to the first housing portion.

The first shaft member and the stator assembly may be fixedly coupled to the second housing portion.

The first shaft member may be fixedly coupled to the housing via an overmold.

The first shaft member may be fixedly coupled to the housing via a press-fit.

As another aspect of the present invention a driven assembly for use in an assembly for moving a fluid is provided. The assembly having: a housing including an inlet and an outlet defined therein; a first shaft member fixedly coupled to the housing, the first shaft member having a central axis; and a stator assembly fixedly coupled to the housing, disposed around the central axis and spaced radially outward from the first shaft member. The driven assembly comprises: a second shaft member having a first end, a second end disposed opposite the first end, and a cylindrical cavity defined therein which extends inward from the first end; a magnetic ring fixedly coupled to the second shaft member at or about the first end; and an arrangement fixedly coupled to the second shaft member at or about the second end. The driven assembly is structured to be rotatably coupled to the first shaft member by a bearing system and rotated about the central axis via magnetic interactions between the stator assembly and the magnetic ring, and the arrangement is structured to cause movement of a fluid into the inlet of the housing and out from the outlet of the housing.

The arrangement may comprise an impeller structured to cause movement of a gas.

As yet another aspect of the present invention a pressure support system for use in providing a flow of breathing gas to the airway of a patient is provided. The pressure support system comprises: a pressure support device having a blower assembly structured to generate the flow of breathing gas; a patient interface structured to be attached to the patient; and a delivery conduit coupled between the pressure support device and the patient interface, the delivery conduit being structured to convey the flow of breathing gas from the pressure support device to the patient interface. The blower assembly comprises: a housing having an inlet and an outlet defined therein; a first shaft member fixedly coupled to the housing, the first shaft member having a central axis; a stator assembly fixedly coupled to the housing, disposed around the central axis and spaced radially outward from the first shaft member. The blower assembly further comprises: a driven assembly comprising: a second shaft member having a first end, a second end disposed opposite the first end, and a cylindrical cavity defined therein which extends inward from the first end, a magnetic ring fixedly coupled to the second shaft member at or about the first end, and an impeller fixedly coupled to the second shaft member at or about the second end, the impeller being structured to cause movement of a gas; and a bearing system disposed between the first shaft member and the second shaft member such that the driven component is rotatably coupled to the first shaft member. The driven assembly is structured to be rotated about the central axis via magnetic interactions between the stator assembly and the magnetic ring.

The housing may comprise a first housing portion and a second housing portion coupled to the first housing portion.

The first shaft member and the stator assembly may be fixedly coupled to the second housing portion.

The first shaft member may be fixedly coupled to the housing via an overmold.

The first shaft member may be fixedly coupled to the housing via a press-fit.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to maintain a constant, fixed orientation relative to each other. As used herein, "selectively coupled" means that two components are coupled in a manner which allows for the components to be readily coupled or uncoupled in a predictable, repeatable manner without damaging either of the components. Unless particularly described otherwise herein, any components which are described merely as being "coupled", may also be "fixedly" or "selectively" coupled without varying from the scope of the present invention.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Aspects of the present invention will be described herein in its application to non-invasive ventilation (NIVV) treatment apparatus (e.g., positive airway pressure (PAP) devices), such as CPAP, but it is to be understood that aspects of the invention may have application to other fields of application where blowers are used, e.g., in both positive pressure and negative pressure applications.

Also, although the example described below is a single stage design, it is of be appreciated that examples of the present invention may be applied to multiple stage designs, e.g., two, three, four, or more stages.

Figure 1:
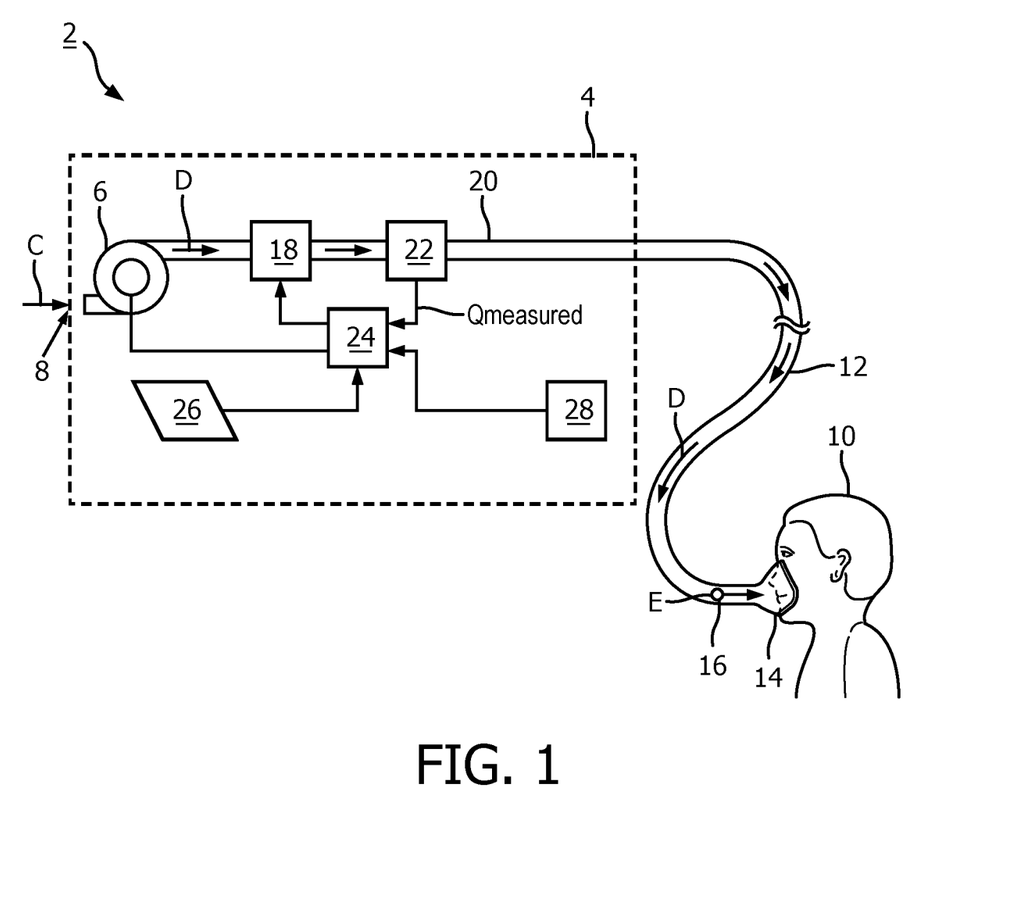
FIG. 1 is a partially schematic view of an airway pressure support system including a pressure generating device in accordance with one example embodiment of the present invention.

An example airway pressure support system 2 according to one particular, non-limiting exemplary embodiment in which the present invention may be implemented is shown in FIG. 1. Airway pressure support system 2 includes a pressure support device 4 which houses a blower assembly 6, an example of which will be described in further detail below. Blower assembly 6 receives breathing gas, generally indicated by arrow C, from the ambient atmosphere through a filtered air inlet 8 provided as part of pressure support device 4, and generates a flow of breathing gas therefrom for delivery to an airway of a patient 10 at relatively higher and lower pressures, i.e., generally equal to or above ambient atmospheric pressure, to generate pressure to provide pressure compensation to patient 10 via a patient circuit 12,14. In the exemplary embodiment, blower assembly 6 is capable of providing a flow of breathing gas ranging in pressure from 4-30 cmH2O. The pressurized flow of breathing gas from blower assembly 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as the patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2.

The present concept also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from blower assembly 6 that is delivered to patient 10. For present purposes, blower assembly 6 and valve 18 are collectively referred to as a pressure generating system because they act in concert to generate and control the pressure and/or flow of gas delivered to patient 10. However, it should be apparent that other techniques for controlling the pressure of the gas delivered to patient 10, such as varying the speed of blower assembly 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to blower assembly 6 alone, and the pressure of gas in the patient circuit is controlled, for example, by controlling the speed of blower assembly 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 28 that detects the pressure of the pressurized fluid in delivery conduit 20. While the point at which the flow is measured by flow sensor 22 and the pressure is measured by pressure sensor 28 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 28 are provided to processing unit 24 to determine the flow of gas at patient 10 ($Q_{PATIENT}$).

An input/output device 26 is provided for setting various parameters used by pressure support system 2, as well as for displaying and outputting information and data to a user, such as a clinician or caregiver.

FIGS. 2-6 illustrate blower assembly 6 which is a single stage blower in accordance with an example embodiment of the present invention. As will be appreciated from the following description, blower assembly 6 provides an arrangement that is relatively compact and lightweight.

Figure 2:
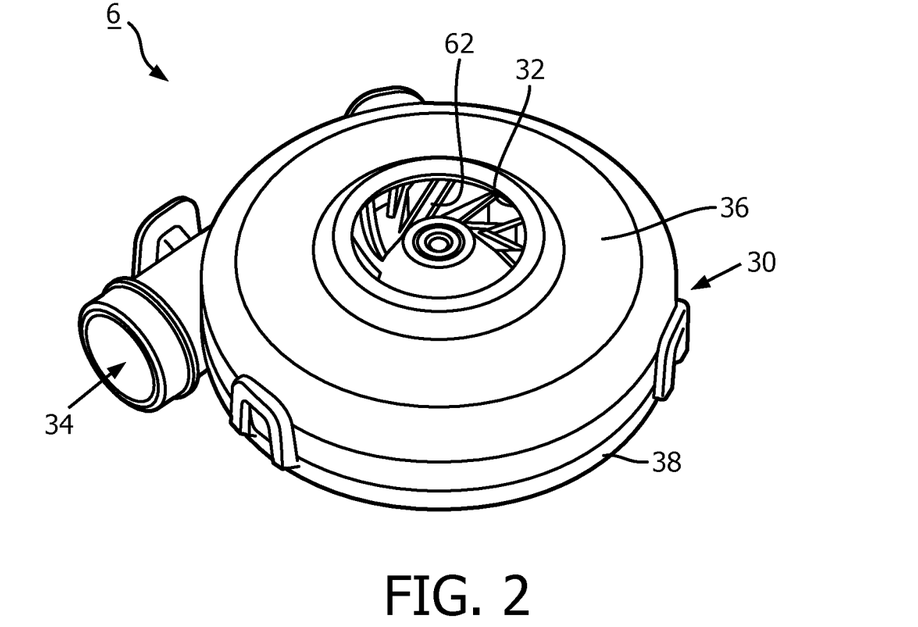
FIG. 2 is a top perspective view of a blower assembly in accordance with one example embodiment of the present invention.
Figure 3:
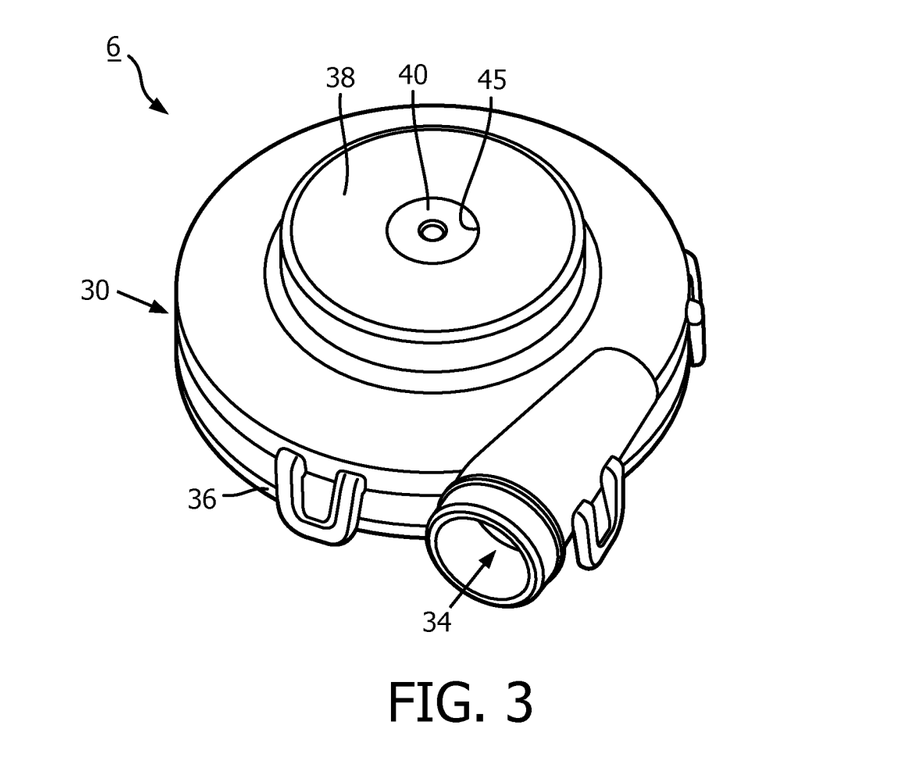
FIG. 3 is a bottom perspective view of the blower assembly of FIG. 2.

Referring first to FIGS. 2 and 3, blower assembly 6 includes a housing 30 (e.g., constructed of metal, plastic (e.g., polycarbonate) or other suitable material) defining a space (not numbered) therein and having an inlet 32 and an outlet 34 defined therein. Blower assembly 6 is operable to draw a supply of gas into housing 30 through inlet 32 and provide a pressurized flow of gas at outlet 34. Blower assembly 6 is of a generally cylindrical shape with inlet 32 aligned with a rotational axis of the assembly and outlet 34 structured to direct gas exiting blower assembly in a generally tangential direction. In the illustrated example, outlet 34 is in the form of an outlet tube that extends outwardly from housing 30, however it is to be appreciated that one or more of the shape, size, and/or orientation of outlet 34 may be varied without varying from the scope of the present invention.

Housing 30 may be formed from a plurality of elements which are formed separately and then subsequently coupled together. In the example embodiment illustrated herein, housing 30 includes a first housing part 36 and a second housing part 38, which are coupled together either selectively (e.g., via a snap-fit or removable fasters) or permanently (e.g., via adhesive, welding, etc.). In such example, inlet 32 is defined in first housing part 36 and outlet 34 is defined in-part by first housing part 36 and in-part by second housing part 38.

Figure 4:
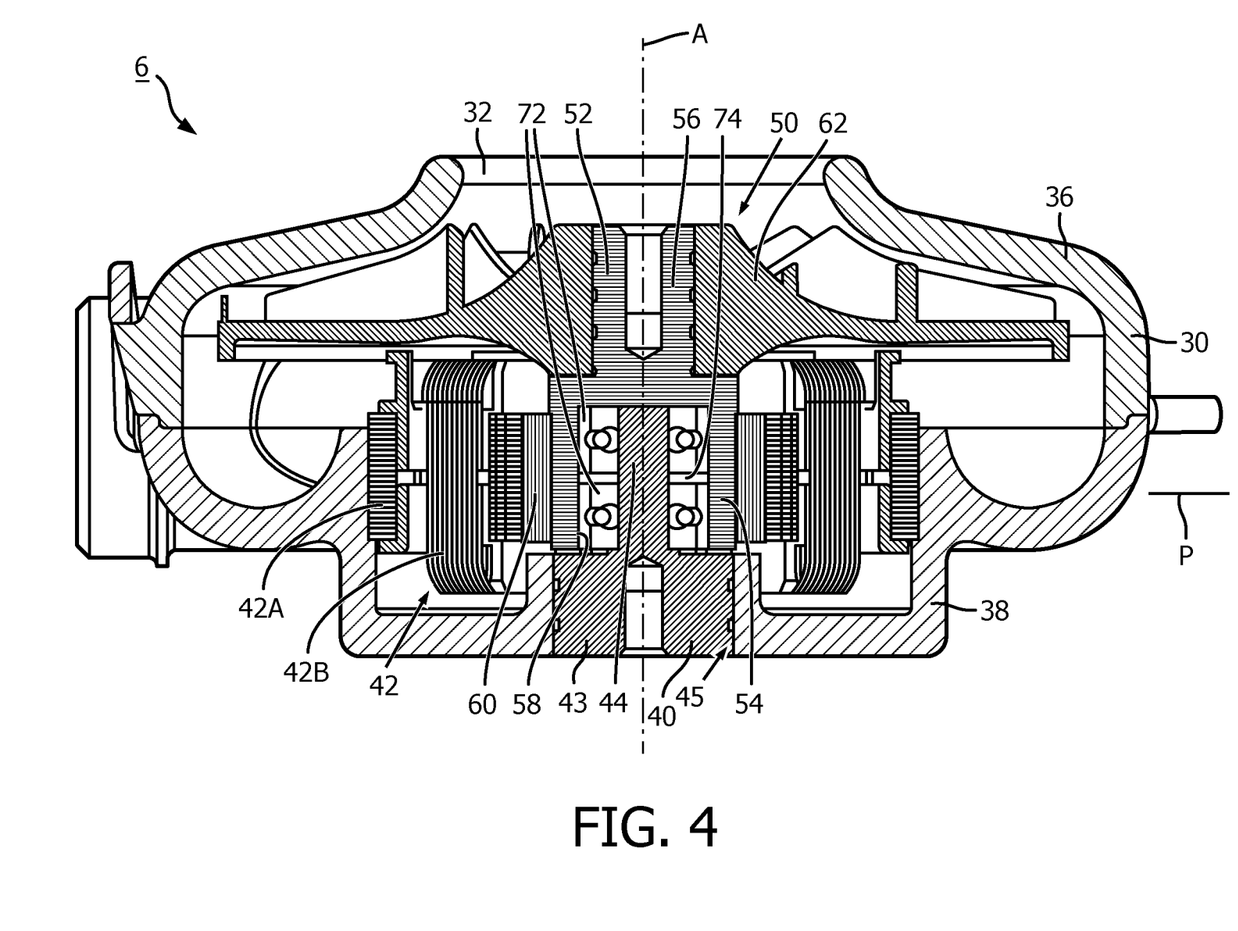
FIG. 4 is a cross-sectional view of the blower assembly of FIG. 2.
Figure 5:
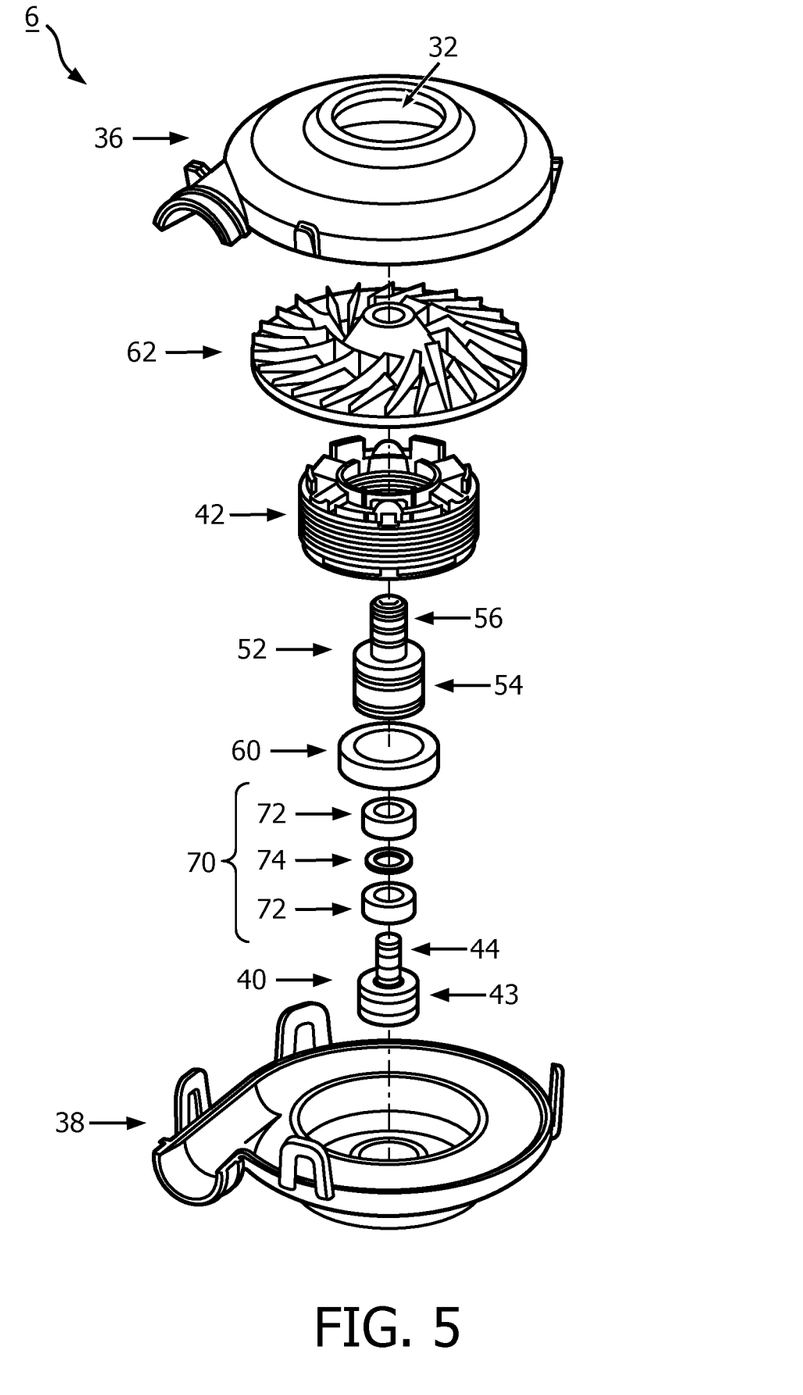
FIGS. 5 and 6, respectively, are exploded, top perspective and sectional elevation, views of the blower assembly of FIG. 2.
Figure 6:
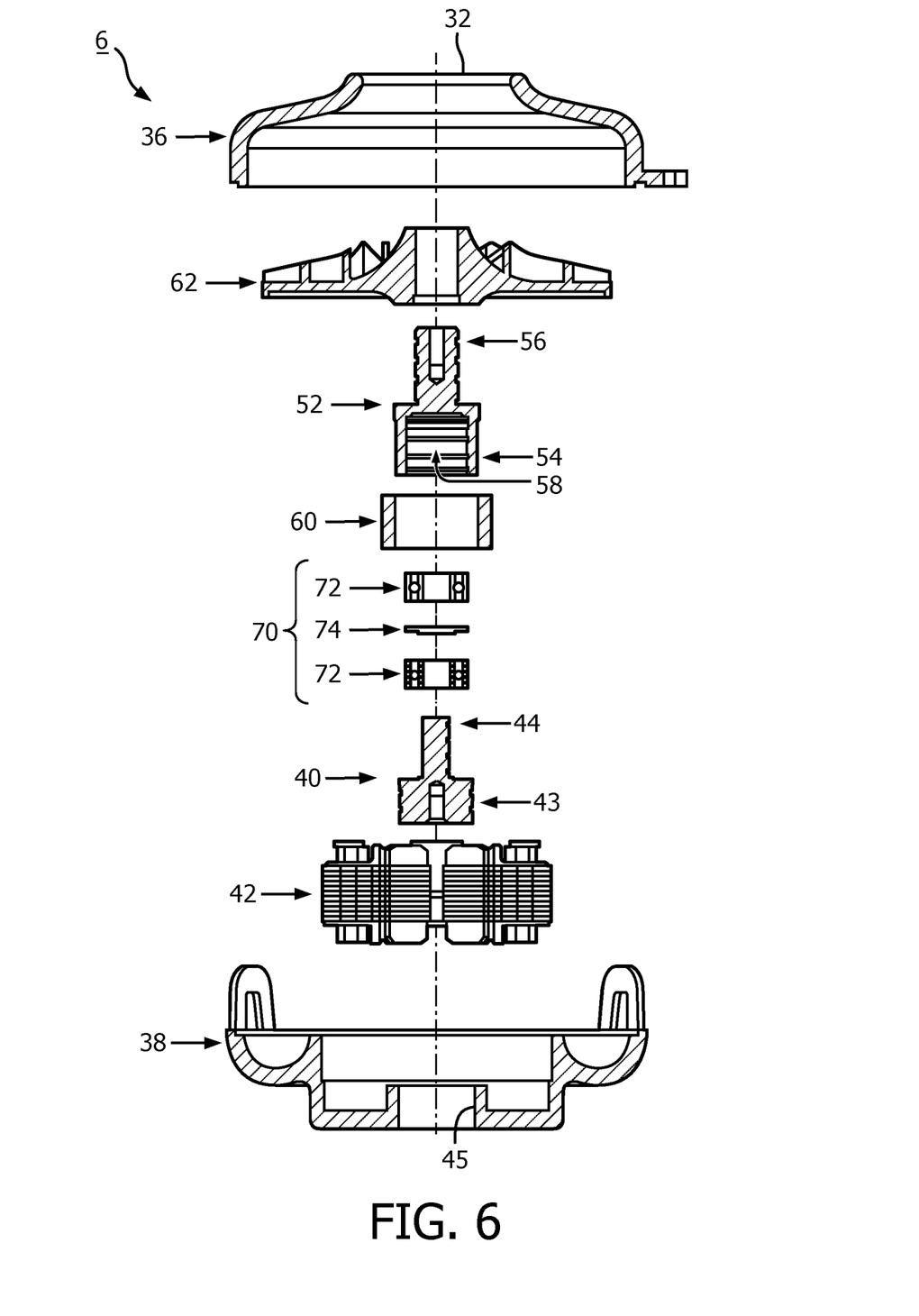

Referring now to FIGS. 4-6, blower assembly further includes a cylindrical first shaft member 40 (e.g., without limitation, formed from steel or other suitable rigid material) and a wound stator assembly 42 having a generally toroidal shape which is disposed around (i.e., so as to encircle) a central axis A of first shaft member 40 and spaced radially outward from first shaft member 40. First shaft member 40 includes a first end 43 fixedly coupled to housing 30 via any suitable arrangement (e.g., via press-fit, over-mold, or other suitable arrangement) and a second end 44, disposed opposite first end 43, which extends into the space within, and defined by housing 30. Stator assembly 42 includes a stator core or electromagnetic core 42A (e.g., including a plurality of laminations stacked on top of one another) on which stator coils or windings 42B are wound. Stator assembly 42 is also fixedly coupled to housing 30 via any suitable arrangement. In the example illustrated embodiment, first shaft member 40 and stator assembly 42 are both fixedly coupled to second housing part 38. More particularly, in the example embodiment illustrated, a portion (not numbered) of first shaft member 40 is disposed in, and coupled to (e.g., via press-fit, over-mold, or other suitable arrangement) a periphery of an aperture 45 defined in second housing part 38 and stator assembly 42 is fixedly coupled to a portion (not numbered) of second housing part 38 outward from aperture 45. Although not shown, it is to be appreciated that stator assembly 42 is structured to be electrically coupled to any suitable source of power and/or control such as commonly provided in the art.

In addition to such components previously described, which may be generally considered as "fixed" components, blower assembly 6 further includes a rotatable or driven assembly 50, which is driven about axis A of first shaft member 40 as discussed further below. Driven assembly 50 includes a second shaft member 52 (e.g., without limitation, formed from steel or other suitable rigid material) having a first end 54, a second end 56 disposed opposite first end 54, and a cylindrical cavity 58 defined therein which extends inward in first end 54. Driven assembly 50 further includes a magnetic ring 60 (e.g., formed from any suitable permanent magnetic material) and an impeller 62 (e.g., formed from any suitable material) which are both fixedly coupled to second shaft member 52. Impeller 62 may be of any suitable configuration for moving air without varying from the scope of the present invention. In the illustrated example embodiment, magnetic ring 60 is fixedly coupled (e.g., via an adhesive or other suitable arrangement) to an outer surface of second shaft member 52 at or about first end 54 such that magnetic ring 60 is disposed radially outward from cavity 58 and impeller 62 is fixedly coupled (e.g., via press-fit or other suitable arrangement) to second shaft member 52 at or about second end 56.

Referring to the sectional view of FIG. 4, driven assembly 50 is rotatably engaged with first shaft member 40 via a bearing system 70 which is disposed in cylindrical cavity 58 of second shaft member 52 and about second end 44 of first shaft member 40. In the example arrangement illustrated in FIGS. 1-6, bearing system 70 includes a number of ball bearings 72 (two are shown in the illustrated embodiment separated by a spacer 74). It is to be appreciated, however, that other types, quantities, and/or arrangements of bearings may be employed as bearing system 70 without varying from the scope of the present invention. It is to be appreciated that such arrangement provides for driven assembly to generally spin freely with respect to first shaft member 40 and housing 30. It is also to be appreciated that such arrangement provides for a generally compact arrangement wherein, moving radially outward from axis A, second end 44 of first shaft member 40, bearing system 70, first end 54 of second shaft member 52, magnetic ring 60 and stator assembly 42 are all disposed in a common plane P, as shown in FIG. 4.

It is to be appreciated that in such arrangement, driven assembly 50 is caused to spin about axis A as a result of interactions between electromagnetic fields produced by stator assembly 42 interaction with magnetic ring 60 of driven assembly 50. It is to be appreciated that the arrangement of driven assembly 50 generally minimizes mass and the distance such mass thereof is from axis A, thus generally minimizing the inertia of driven assembly 50. As a result, driven assembly 50 provides for a faster response time than conventional designs.

Figure 7:
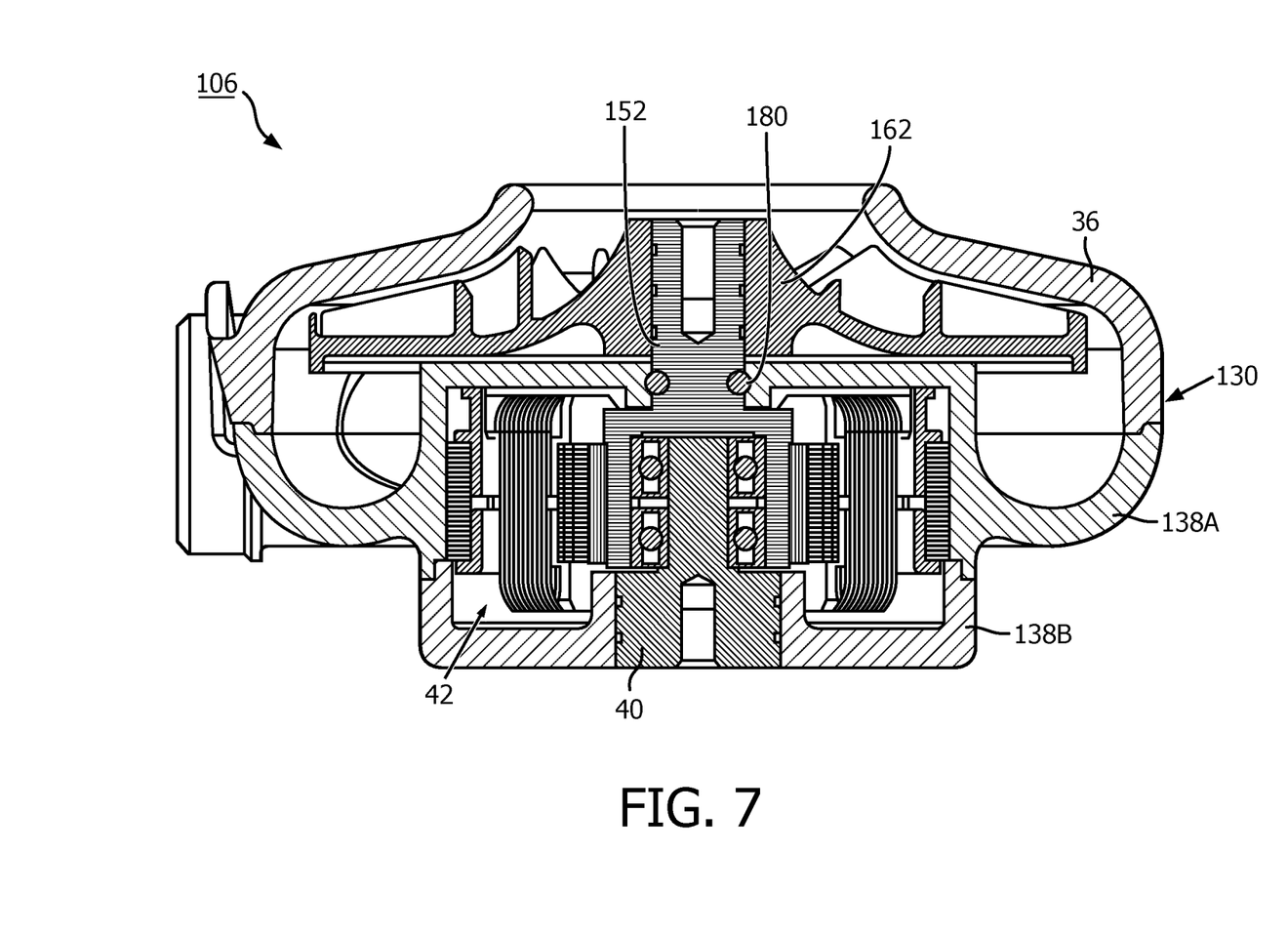
FIG. 7 is a cross-sectional view of an assembly for moving a liquid in accordance with another example embodiment of the present invention.

Although exemplified as a blower assembly herein, it is to be appreciated that embodiment of the present invention may also be employed in other fluid moving devices, such as those used for moving liquids. FIG. 7 shows a sectional view of an assembly 106 for use in a fluid moving application in accordance with an example embodiment of the present invention. Assembly 106 is of a similar arrangement as blower assembly 6 and utilizes similar components with a few distinctions. One such distinction is that blower assembly includes a housing 130 which is formed from three different parts: first housing part 36 (similar to that of assembly 6), a second housing part 138A, and a third housing part 138B. Second and third housing parts 138A and 138B function similarly as second housing part 38 of assembly 6, while also providing a sealed housing in which stator assembly 42 is disposed. Such sealed housing is generally accomplished by sealing second housing part 138A about a second shaft member 152 (formed and positioned similarly as second shaft member 52 of assembly 6) via a sealing mechanism 180. An impeller 162, which is structured to move a liquid, is rigidly coupled to second shaft member 152 outside of the sealed housing defined by second housing part 138A and third housing part 138B.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. An assembly for moving a fluid, the assembly comprising:
    a housing having an inlet and an outlet defined therein;
    a first shaft member having a first end fixedly coupled to the housing, a second end disposed opposite the first end, and a central axis (A);
    a stator assembly fixedly coupled to the housing, disposed around the central axis and spaced radially outward from the first shaft member;
    a driven assembly comprising:
        a second shaft member having a first end, a second end disposed opposite the first end, and a cylindrical cavity defined within the second shaft member which extends inward from the first end alone, and does not extend within the second end,
        a magnetic ring fixedly coupled to the second shaft member at or about the first end, and
        an arrangement fixedly coupled to the second shaft member at or about the second end; and
    a bearing system disposed between the second end of the first shaft member and the first end of the second shaft member such that the driven assembly is rotatably coupled to the housing via the first shaft member at the second end of the first shaft member alone,
    wherein the driven assembly is structured to be rotated about the central axis via magnetic interactions between the stator assembly and the magnetic ring, and
    wherein the arrangement is structured to cause movement of a fluid into the inlet of the housing and out from the outlet of the housing.

2. The assembly of claim 1, wherein the arrangement comprises an impeller structured to cause movement of a gas.

3. The assembly of claim 1, wherein the housing comprises a first housing portion and a second housing portion coupled to the first housing portion.

4. The assembly of claim 3, wherein the first shaft member and the stator assembly are fixedly coupled to the second housing portion.

5. The assembly of claim 1, wherein the first shaft member is fixedly coupled to the housing via an overmold.

6. The assembly of claim 1, wherein the first shaft member is fixedly coupled to the housing via a press-fit.

7. The assembly of claim 1, wherein, moving radially outward from the central axis (A), the second end of the first shaft member, the bearing system, the first end of the second shaft member, the magnetic ring, and the stator assembly are all disposed in a common plane (P) which is perpendicular to the central axis.

8. The assembly of claim 1, wherein the stator assembly comprises a wound stator assembly of stator coils or windings having a toroidal shape which is disposed around the central axis of the first shaft member and spaced radially outward from the first shaft member, and wherein the stator assembly further comprises a stator core on which the stator coils or windings are wound.

9. The assembly of claim 1, wherein the fluid comprises a liquid, and wherein the housing comprises at least three different parts, a first housing part, a second housing part, and a third housing part, wherein the second and third housing parts provide a sealed housing in which the stator assembly is disposed, further wherein second housing part includes a sealing mechanism disposed about the second shaft member, wherein the arrangement is rigidly coupled to the second shaft member outside of the sealed housing.

10. A driven assembly for use in an assembly for moving a fluid, the assembly having: a housing including an inlet and an outlet defined therein; a first shaft member having a first end fixedly coupled to the housing, a second end disposed opposite the first end, and a central axis (A); and a stator assembly fixedly coupled to the housing, disposed around the central axis and spaced radially outward from the first shaft member, the driven assembly comprising:
    a second shaft member having a first end, a second end disposed opposite the first end, and a cylindrical cavity defined within the second shaft member which extends inward from the first end alone, and does not extend within the second end,
    a magnetic ring fixedly coupled to the second shaft member at or about the first end, and
    an arrangement fixedly coupled to the second shaft member at or about the second end,
    wherein the driven assembly is structured to be rotatably coupled to the housing via the first shaft member at the second end of the first shaft member alone, further by a bearing system disposed between the second end of the first shaft member and the first end of the second shaft member, and rotated about the central axis via magnetic interactions between the stator assembly and the magnetic ring, and
    wherein the arrangement is structured to cause movement of a fluid into the inlet of the housing and out from the outlet of the housing.

11. The driven assembly of claim 10, wherein the arrangement comprises an impeller structured to cause movement of a fluid.

12. The driven assembly of claim 10, wherein, moving radially outward from the central axis (A), the second end of the first shaft member, the bearing system, the first end of the second shaft member, the magnetic ring, and the stator assembly are all disposed in a common plane (P) which is perpendicular to the central axis.

13. The driven assembly of claim 10, wherein the stator assembly comprises a wound stator assembly of stator coils or windings having a toroidal shape which is disposed around the central axis of the first shaft member and spaced radially outward from the first shaft member, and wherein the stator assembly further comprises a stator core on which the stator coils or windings are wound.

14. A pressure support system for use in providing a flow of breathing gas to the airway of a patient, the pressure support system comprising:
    a pressure support device having a blower assembly structured to generate the flow of breathing gas;
    a patient interface structured to be attached to the patient; and
    a delivery conduit coupled between the pressure support device and the patient interface, the delivery conduit being structured to convey the flow of breathing gas from the pressure support device to the patient interface, wherein the blower assembly comprises:
   a housing having an inlet and an outlet defined therein;
   a first shaft member having a first end fixedly coupled to the housing, a second end disposed opposite the first end, and a central axis (A);
   a stator assembly fixedly coupled to the housing, disposed around the central axis and spaced radially outward from the first shaft member;
   a driven assembly comprising:
      a second shaft member having a first end, a second end disposed opposite the first end, and a cylindrical cavity defined within the second shaft member which extends inward from the first end alone, and does not extend within the second end,
      a magnetic ring fixedly coupled to the second shaft member at or about the first end, and
      an impeller fixedly coupled to the second shaft member at or about the second end, the impeller being structured to cause movement of a gas into the inlet of the housing and out from the outlet of the housing; and
   a bearing system disposed between the second end of the first shaft member and the first end of the second shaft member such that the driven assembly is rotatably coupled to the housing via the first shaft member at the second end of the first shaft member alone, wherein the driven assembly is structured to be rotated about the central axis via magnetic interactions between the stator assembly and the magnetic ring.

15. The pressure support system of claim 14, wherein the housing comprises a first housing portion and a second housing portion coupled to the first housing portion.

16. The pressure support system of claim 15, wherein the first shaft member and the stator assembly are fixedly coupled to the second housing portion.

17. The pressure support system of claim 14, wherein the first shaft member is fixedly coupled to the housing via an overmold.

18. The pressure support system of claim 14, wherein the first shaft member is fixedly coupled to the housing via a press-fit.

19. The pressure support system of claim 14, wherein, moving radially outward from the central axis (A), the second end of the first shaft member, the bearing system, the first end of the second shaft member, the magnetic ring, and the stator assembly are all disposed in a common plane (P) which is perpendicular to the central axis.

20. The pressure support system of claim 14, wherein the stator assembly comprises a wound stator assembly of stator coils or windings having a toroidal shape which is disposed around the central axis of the first shaft member and spaced radially outward from the first shaft member, and wherein the stator assembly further comprises a stator core on which the stator coils or windings are wound.

* * * * *